United States Patent
Ley et al.

(10) Patent No.: US 7,411,082 B2
(45) Date of Patent: Aug. 12, 2008

(54) SYNTHESIZING METHOD FOR COMPOUND, AND CATALYST FOR SYNTHESIS REACTION

(75) Inventors: Steven V. Ley, Cambridge (GB); Martin D. Smith, Cambridge (GB); Chandrashekar Ramarao, Hyderabad (IN); Antonia F. Stepan, Cambridge (GB); Hirohisa Tanaka, Osaka (JP)

(73) Assignees: Cambridge University Technical Services Ltd., Cambridge (GB); Daihatsu Motor Co., Ltd, Osaka (JP)

( * ) Notice: Subject to any disclaimer, the term of this patent is extended or adjusted under 35 U.S.C. 154(b) by 573 days.

(21) Appl. No.: 10/951,607

(22) Filed: Sep. 29, 2004

(65) Prior Publication Data
US 2005/0215804 A1 Sep. 29, 2005

(30) Foreign Application Priority Data
Mar. 29, 2004 (JP) .............................. 2004-094189

(51) Int. Cl.
*C07F 17/02* (2006.01)
(52) U.S. Cl. .............................. 556/136; 556/7; 556/81
(58) Field of Classification Search .................... 556/7, 556/136
See application file for complete search history.

(56) References Cited

U.S. PATENT DOCUMENTS

| | | | |
|---|---|---|---|
| 5,210,211 A | 5/1993 | Hodges et al. | |
| 5,389,659 A | 2/1995 | Ross et al. | |
| 2003/0171625 A1 | 9/2003 | Ishii et al. | |
| 2006/0106261 A1 | 5/2006 | Ishii et al. | |

FOREIGN PATENT DOCUMENTS

| | | |
|---|---|---|
| JP | 06-25175 | 2/1994 |
| JP | 06-508370 | 9/1994 |
| JP | 10-114691 | 5/1998 |
| JP | 2003-327547 | 11/2003 |

OTHER PUBLICATIONS

Mio, M.J., et al., One-Pot Synthesis of Symmetrical and Unsymmetrical Cisarylethynes by a Modification of the Sonogashira Coupling Reaction, Aug. 30, 2002, Organic Letters, vol. 4, No. 19, pp. 3199-3202.*

Miyaura, Norio and Suzuki, Akira, Palladium-Catalyzed Cross-Coupling Reactions of Organoboron Compounds, Chemical Reviews, vol. 95, No. 7, pp. 2457-2483, 1995.

Smith, M.D., Stepan, A.F., Ramarao, C., Brennan, P.E., and Ley, S.V., Sep. 2003 Palladium-containing perovskites: recoverable and reuseable catalysts for Suzuki couplings.

* cited by examiner

*Primary Examiner*—Zinna N Davis
(74) *Attorney, Agent, or Firm*—Jean C. Edwards, Esq.; Akerman Senterfitt

(57) ABSTRACT

A catalyst for synthesis reaction that can allow the cross coupling reaction at an improved yield, and yet can be collected after used for the reaction and recycled, and a synthesizing method for a compound using the same catalyst for synthesis reaction. In the Suzuki cross-couplings given by the following reaction formula (15), palladium containing perovskite-like composite oxide is used as a catalyst for synthesis reaction:

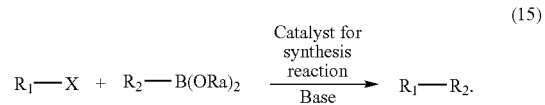

(15)

5 Claims, No Drawings

SYNTHESIZING METHOD FOR COMPOUND, AND CATALYST FOR SYNTHESIS REACTION

This application claims priority from Japanese Patent Application No. 2004-094189, filed Mar. 29, 2004, the entire contents of which are herein incorporated by reference to the extent allowed by law.

BACKGROUND OF THE INVENTION

1. Field of the Invention

The present invention relates to a synthesizing method for a compound and to a catalyst for synthesis reaction. More particularly, the present invention relates to a synthesizing method for a compound by using a cross coupling reaction and to a catalyst for synthesis reaction used in that synthesizing method.

2. Description of the Prior Art

Cross-coupling reactions are the reaction to bond two compounds together. Of the cross-coupling reactions, the Suzuki cross-couplings, the Stille cross-couplings and the Heck cross-couplings are generally known as the cross coupling reaction using palladium as a catalyst for synthesis reaction.

For example, the Suzuki cross-couplings, which has a number of advantages of, for example, producing the synthesis of unsymmetrical biphenyl compounds without reacting with co-existing functional groups, permitting the reaction to proceed in the presence of water, and reducing the production of poisonous by-products, are widely used for synthesis of organic compounds having biphenyl skeletons and effectively used for the synthesis of e.g. medical products and the like (e.g. JP Laid-open (Unexamined) Patent Publication No. Hei 6-25175 and JP Publish No. Hei 6-508370 in Official Gazette publishing Japanese translation of PCT patent application).

In the Suzuki cross-couplings, palladium used as the catalyst for synthesis reaction is usually used in the form of an organic metal complex soluble in an organic solvent, such as tetrakis (triphenylphosphine) palladium.

Palladium is expensive and valuable and accordingly is desired to be collected after used for the reaction and recycled, for reduction in manufacturing cost.

However, in the practical reaction, palladium is used in the form of the organic metal complex soluble in the organic solvent, such as tetrakis (triphenylphosphine) palladium, as mentioned above. Due to this, it is practically difficult to collect the palladium after used for the reaction, so that the palladium is, in fact, wasted without being collected after used for the reaction.

SUMMARY OF THE INVENTION

It is an object of the invention to provide a catalyst for synthesis reaction that can allow the cross coupling reaction at an improved yield, and yet can be collected after used for the reaction and recycled. It is another object of the invention to provide a synthesizing method for a compound using the same catalyst for synthesis reaction.

The present invention provides a synthesizing method for a compound, wherein a compound indicated in a general formula (1) given below, and a compound indicated in a general formula (2) given below or a compound indicated in a general formula (3) given below are allowed to react with each other in the presence of a perovskite-like composite oxide comprising palladium:

$$R_1-X \quad (1)$$

(In the formula, $R_1$ represents an aryl group that may have a substituent, a heterocyclic group that may have a substituent, or an alkenyl group that may have a substituent, and X represents a halogen atom, a trifluoromethanesulfonyloxy group, a p-toluenesulfonyloxy group, or a methanesulfonyloxy group.)

$$R_2\text{-M} \quad (2)$$

(In the formula, $R_2$ represents an aryl group that may have a substituent, a heterocyclic group that may have a substituent, or an alkenyl group that may have a substituent, M represents a $—B(ORa)_2$ group or a $—Sn(Rb)_3$ group, Ra represents a hydrogen atom or an alkyl group that may have a substituent, and Rb represents an alkyl group. As a substitute for Ra, an arylene group that may have a substituent or an alkylene group that may have a substituent may be used as a bonding hand of —OBO—, to form a ring including the —OBO—.)

$$R_3HC=CR_4R_5 \quad (3)$$

(In the formula, $R_3$, $R_4$, and $R_5$ each represent a hydrogen atom, an alkyl group that may have a substituent, an aryl group that may have a substituent, a carboxylic acid derivative, an acid amide derivative, or a cyano group.)

In the synthesizing method for a compound, it is preferable that the compound indicated in the general formula (1) and the compound indicated in the general formula (2) are allowed to react with each other in the presence of the perovskite-like composite oxide comprising palladium. In the general formula (1), $R_1$ is an aryl group that may have a substituent, and X is a halogen atom, and in the general formula (2), $R_2$ is an aryl group that may have a substituent, and M is a $—B(ORa)_2$ group.

In the synthesizing method for a compound, it is preferable that the perovskite-like composite oxide comprising palladium is represented by a general formula (4) given below, or by a general formula (5) given below, especially by a general formula (6) given below:

$$AB_{1-x}Pd_xO_3 \quad (4)$$

(In the formula, A represents at least one element selected from the group consisting of rare-earth elements and alkaline-earth metals, B represents at least one element selected from the group consisting of transition elements except for rare-earth elements and Pd; and Al, and x represents an atomic rate of Pd.)

$$A_{1-y}A'_yB_{1-x}Pd_xO_3 \quad (5)$$

(In the formula, A represents at least one element selected from rare-earth elements, A' represents at least one element selected from alkaline-earth metals, B represents at least one element selected from the group consisting of transition elements except for rare-earth elements and Pd; and Al, x represents an atomic rate of Pd, and y represents an atomic rate of $0 \leq y \leq 0.5$.)

$$AB_{1-x}Pd_xO_3 \quad (6)$$

(In the formula, A represents at least one element selected from the group consisting of Y, La, Ce, Pr and Nd, B represents at least one element selected from the group consisting of Mn, Fe, Co and Al, and x represents an atomic rate of Pd.)

The present invention covers a catalyst for synthesis reaction comprising a perovskite-like composite oxide comprising palladium and used to allow a compound indicated in a general formula (1) given below, and a compound indicated in a general formula (2) given below or a compound indicated in a general formula (3) given below to react with each other:

$$R_1-X \qquad (1)$$

(In the formula, $R_1$ represents an aryl group that may have a substituent, a heterocyclic group that may have a substituent, or an alkenyl group that may have a substituent, and X represents a halogen atom, a trifluoromethanesulfonyloxy group, a p-toluenesulfonyloxy group, or a methanesulfonyloxy group.)

$$R_2\text{-M} \qquad (2)$$

(In the formula, $R_2$ represents an aryl group that may have a substituent, a heterocyclic group that may have a substituent, or an alkenyl group that may have a substituent, M represents a $-B(ORa)_2$ group or a $-Sn(Rb)_3$ group, Ra represents a hydrogen atom or an alkyl group that may have a substituent, and Rb represents an alkyl group. As a substitute for Ra, an arylene group that may have a substituent or an alkylene group that may have a substituent may be used as a bonding hand of —OBO—, to form a ring including the —OBO—.)

$$R_3HC=CR_4R_5 \qquad (3)$$

(In the formula, $R_3$, $R_4$, and $R_5$ each represent a hydrogen atom; an alkyl group that may have a substituent, an aryl group that may have a substituent, a carboxylic acid derivative, an acid amide derivative, or a cyano group.)

The catalyst for synthesis reaction of the present invention is suitably used for allowing the compound indicated in the general formula (1) and the compound indicated in the general formula (2) to react with each other, where in the general formula (1), $R_1$ is an aryl group that may have a substituent, and X is a halogen atom, and in the general formula (2), $R_2$ is an aryl group that may have a substituent, and M is a $-B(ORa)_2$ group.

It is preferable that the catalyst for synthesis reaction of the present invention is represented by a general formula (4) given below: or by a general formula (5) given below, especially by a general formula (6) given below:

$$AB_{1-x}Pd_xO_3 \qquad (4)$$

(In the formula, A represents at least one element selected from the group consisting of rare-earth elements and alkaline-earth metals, B represents at least one element selected from the group consisting of transition elements except for rare-earth elements and Pd; and Al, and x represents an atomic rate of Pd.)

$$A_{1-y}A'_yB_{1-x}Pd_xO_3 \qquad (5)$$

(In the formula, A represents at least one element selected from rare-earth elements, A' represents at least one element selected from alkaline-earth metals, B represents at least one element selected from the group consisting of transition elements except for rare-earth elements and Pd; and Al, x represents an atomic rate of Pd, and y represents an atomic rate of $0 \leq y \leq 0.5$.)

$$AB_{1-x}Pd_xO_3 \qquad (6)$$

(In the formula, A represents at least one element selected from the group consisting of Y, La, Ce, Pr and Nd, B represents at least one element selected from the group consisting of Mn, Fe, Co and Al, and x represents an atomic rate of Pd.)

In the synthesizing method for compound of the present invention, the compound can be synthesized at an improved yield by the cross-couplings in the presence of the perovskite-like composite oxide comprising palladium. Also, the perovskite-like composite oxide comprising palladium can be collected after completion of the reaction and also recycled.

The catalyst for synthesis reaction of the present invention is used effectively as the catalyst for synthesis reaction in the cross-coupling. Also, it can provide an improved yield in the cross-coupling reaction, and yet can be collected after the reaction and also recycled, thus providing reduction of the manufacturing costs.

DETAILED DESCRIPTION OF THE PREFERRED EMBODIMENT

A catalyst for synthesis reaction of the present invention comprises a perovskite-like composite oxide comprising palladium (Pd).

The perovskite-like composite oxide comprising palladium used herein refers to a composite oxide having a perovskite-like structure represented by the general formula $ABO_3$. Any perovskite-like composite oxide may be used without being limited to any particular type one, as long as it comprises palladium.

The perovskite-like composite oxides comprising palladium include, for example, a perovskite-like composite oxide that contains palladium as a component of such composition that palladium can be a constituent element of the perovskite-like composite oxide, and a palladium supported perovskite-like composite oxide such that palladium is supported later on the perovskite-like composite oxide.

The perovskite-like composite oxide that contains a palladium as a component of the composition are represented by general formula (4) given below:

$$AB_{1-x}Pd_xO_3 \qquad (4)$$

(In the formula, A represents at least one element selected from the group consisting of rare-earth elements and alkaline-earth metals, B represents at least one element selected from the group consisting of transition elements except for rare-earth elements and Pd; and Al, and x represents an atomic rate of Pd.)

In the general formula (4), the rare-earth elements represented by A include, for example, Sc (scandium), Y (yttrium), La (lanthanum), Ce (cerium), Pr (praseodymium), Nd (neodymium), Pm (promethium), Sm (samarium), Eu (europium), Gd (gadolinium), Tb (terbium), Dy (dysprosium), Ho (holmium), Er (erbium), Tm (thulium), Yb (ytterbium), and Lu (lutetium). Y, La, Ce, Pr and Nd can be cited as the preferable ones.

These rare-earth elements may be used alone or in combination of two or more.

In the general formula (4), the alkaline-earth metals represented by A include, for example, Be (beryllium), Mg (magnesium), Ca (calcium), Sr (strontium), Ba (barium), and Ra (radium).

The alkaline-earth metals may be used alone or in combination of two or more.

In the general formula (4), it is preferable that an atomic rate of the alkaline-earth metal to the rare-earth element is not more than 0.5 for A. It is further preferable that the rare-earth element is used alone for A.

In the general formula (4), the transition elements (except for the rare-earth elements and Pd) represented by B include, for example, the elements 22 (atomic number) (Ti) through 30 (atomic number) (Zn), the elements 40 (atomic number) (Zr) through 48 (atomic number) (Cd), and the elements 72 (atomic number) (Hf) through 80 (atomic number) (Hg) of the periodic table (IUPAC, 1990) (except for Pd).

The transition elements (except for the rare-earth elements and Pd), and Al represented by B include, for example, Cr (chromium), Mn (manganese), Fe (iron), Co (cobalt), Ni (nickel), Cu (copper), Zn (zinc), and Al (aluminum). Mn, Fe, Co, and Al can be cited as the preferable ones.

The perovskite-like composite oxides containing palladium as a component of the composition can be produced by any proper method for preparing the composite oxide, such as a coprecipitation method, a citrate complex method, and an alkoxide method, without being limited to any particular method.

In the coprecipitation method, a mixed aqueous salt solution containing salts of the elements listed above in a prescribed stoichiometric ratio is prepared. Then, the mixed aqueous salt solution is coprecipitated by adding a neutralizing agent thereto and/or adding the mixed aqueous salt solution to the neutralizing agent. Thereafter, the coprecipitate thus obtained is dried and then heat-treated.

The salts of the elements used include, for example, inorganic salts, such as sulfate, nitrate, chloride, and phosphate, and organic salts, such as acetate and oxalate. The mixed aqueous salt solution can be prepared, for example, by adding the salts of the elements to water in such a proportion as to establish a prescribed stoichiometric ratio and mixing them with stirring.

Thereafter, the mixed aqueous salt solution thus prepared is coprecipitated by adding the neutralizing agent thereto. This coprecipitate can also be obtained by dropping the mixed aqueous salt solution into a solution containing a surplus neutralizing agent little by little. The neutralizing agents used include, for example, ammonia, organic bases of amines, such as a triethylamine and a pyridine, and inorganic bases, such as caustic soda, caustic potash, potassium carbonate and ammonium carbonate. It should be noted that the neutralizing agent is added to the solution so that the pH value of the solution after the addition of the neutralizing agent can be in the range of the order of 6-14, or preferably 8-12.

Then, the coprecipitate thus obtained is washed with water, if necessary, and is dried, for example, by vacuum drying or circulation drying. Thereafter, it is heat-treated at a temperature in the range of e.g. about 400° C. to about 1,000° C., or preferably about 600° C. to about 950° C. The perovskite-like composite oxides can be obtained in the manner as described above.

In the citrate complex method, for example, a citrate complex mixed aqueous salt solution containing a citrate complex and salts of the elements listed above so that the salts of the elements can have a prescribed stoichiometric ratio is prepared, first. Then, the citrate complex mixed aqueous salt solution is solidified by drying, to form the citrate complex of the elements listed above. Thereafter, the citrate complex thus obtained is provisionally baked and then heat-treated.

The same as the salts listed above can be used as the salts of the elements used. Also, the citrate complex mixed aqueous salt solution can be prepared, for example, by preparing the mixed aqueous salt solution in the same manner as above, first, and, then, adding a citrate solution into the mixed aqueous salt solution.

Thereafter, the citrate complex mixed aqueous salt solution obtained is solidified by drying, to form the citrate complex of the elements listed above. The solidification of the citrate complex mixed aqueous salt solution by drying is carried out at a temperature at which the citrate complex to be formed is not decomposed, or at a temperature of the order of room temperature to 150° C., to remove fluid from the solution immediately. The citrate complex of the elements listed above can be formed in this manner.

Then, the citrate complex formed is provisionally baked and then heat-treated. The provisional baking is carried out, for example, by heating the citrate complex at 250° C. or more under vacuum or under an inert atmosphere. Thereafter, it is heat-treated at a temperature in the range of e.g. about 400° C. to about 1,000° C., or preferably about 600° C. to about 950° C. The perovskite-like composite oxides can be obtained in the manner as described above.

In the alkoxide method, for example, an alkoxide mixed solution containing alkoxide of the elements listed above, except for noble metals including Pd, in a prescribed stoichiometric ratio is prepared, first. Then, the alkoxide mixed solution prepared is precipitated on hydrolysis by adding an aqueous solution containing salts of the noble metals including Pd into the alkoxide mixed solution. Thereafter, the precipitate obtained is dried and then heat-treated.

The alkoxides of the respective elements include, for example, alcoholate formed by the respective elements and alkoxy, such as methoxy, ethoxy, propoxy, isopropoxy, and butoxy, and alcoxyalcoholate of the elements given by general formula (7) given below:

E[OCH(R$_6$)—(CH$_2$)$_i$—OR$_7$]j  (7)

(In the formula, E represents the respective elements listed above, R$_6$ represents a hydrogen atom or alkyl groups with carbon numbers between 1 and 4, R$_7$ represents alkyl groups with carbon numbers between 1 and 4, i represents integers between 1 and 3, and j represents integers between 2 and 3.)

To be more specific, the alcoxyalcoholates include, for example, methoxyethylate, methoxypropylate, methoxybutylate, ethoxyethylate, ethoxypropylate, propoxyethylate, and butoxyethylate.

Then, an alkoxide mixed aqueous solution can be prepared, for example, by adding the alkoxides of the respective elements to an organic solvent in such a proportion as to establish the prescribed stoichiometric ratio mentioned above and mixing them with stirring.

No particular limitation is imposed on the organic solvents, as long as they can dissolve the alkoxides of the respective elements. For example, aromatic hydrocarbons, aliphatic hydrocarbons, alcohols, ketones and esters may be used as the organic solvent. Aromatic hydrocarbons, such as benzene, toluene, and xylene, is preferably used.

Thereafter, the alkoxide mixed solution prepared is precipitated by adding an aqueous solution containing salts of the noble metals including Pd into the alkoxide mixed solution. The aqueous solution containing salts of the noble metals including Pd include, for example, nitrate solution, chloride solution, hexaammine chloride solution, dinitrodiammine nitrate solution, hexachloro acid hydrate, and potassium cyanide salt.

Then, the precipitate obtained is dried, for example, by vacuum drying or circulation drying and then heat-treated at a temperature in the range of e.g. about 400° C. to about 1,000° C., or preferably about 500° C. to about 850° C. The perovskite-like composite oxides can be obtained in the manner as described above.

In the alkoxide method, the alkoxide mixed solution may alternatively be prepared in the following manner. For example, a solution containing organic metallic salts of the noble metals including Pd is mixed in the above-said alkoxide mixed solution, to prepare homogeneous mixed solution, first. Then, the homogeneous mixed solution thus prepared is precipitated by adding water into it. Then, the precipitate obtained is dried and then heat-treated.

The organic metallic salts of the noble metals including Pd include, for example, metal chelate complexes of the noble metals including Pd, such as carboxylate of the noble metals including Pd formed from acetate salt, propionate salt, etc., and diketone complexes of the noble metals including Pd formed from diketone compounds indicated in general formula (8) or (9) given below:

$$R_8COCHR_{10}COR_9 \tag{8}$$

(In the formula, $R_8$ represents alkyl groups with carbon numbers between 1 and 4, or fluoroalkyl groups with carbon numbers between 1 and 4 or aryl groups, $R_9$ represents alkyl groups with carbon numbers between 1 and 4, fluoroalkyl groups with carbon numbers between 1 and 4 or aryl groups, or alkyloxy groups with carbon numbers between 1 and 4, and $R_{10}$ represents hydrogen atom or alkyl groups with carbon numbers between 1 and 4.)

$$CH_3CH(COR_{11})_2 \tag{9}$$

(In the formula, $R_{11}$ represents a hydrogen atom or alkyl groups with carbon numbers between 1 and 4.)

In the general formulas (8) and (9) given above, the alkyl groups with carbon numbers between 1 and 4 of $R_8$, $R_9$, $R_{10}$ and $R_{11}$ include, for example, methyl, ethyl, propyl, isopropyl, n-butyl, s-butyl, and t-butyl. The fluoroalkyl groups with carbon numbers between 1 and 4 of $R_8$ and $R_9$ include, for example, trifluoromethyl. The aryl groups of $R_8$ and $R_9$ include, for example, phenyl. The alkyloxy groups with carbon numbers between 1 and 4 of $R_9$ include, for example, methoxy, ethoxy, propoxy, isopropoxy, n-butoxy, s-butoxy, and t-butoxy.

The diketone compounds include, specifically, for example 2,4-pentanedione, 2,4-hexanedione, 2,2,-dimethyl-3,5-hexanedione, 1-phenyl-1,3-butanedione, 1-trifluoromethyl-1,3-butanedione, hexafluoro acetylacetone, 1,3-diphenyl-1,3-propanedione, dipivaloylmethane, methylacetoacetate, ethylacetoacetate, and t-butylacetoacetate.

The solution of the organic metallic salts of the noble metals including Pd can be prepared, for example, by adding the organic metallic salts of the noble metals including Pd into an organic solvent in such a proportion as to establish a prescribed stoichiometric ratio and mixing them with stirring. The same organic solvent as above can be used as the organic solvent.

Thereafter, the solution containing the organic metallic salts of the noble metals including Pd thus prepared is mixed in the above-said alkoxide mixed solution, to prepare homogeneous mixed solution. Then, the homogeneous mixed solution thus prepared is precipitated by adding water into it. Then, the precipitate obtained is dried, for example, by vacuum drying or circulation drying and then heat-treated at a temperature in the range of e.g. about 400° C. to about 1,000° C., or preferably about 500° C. to about 850° C. The perovskite-like composite oxides can be obtained in this manner.

The perovskite-like composite oxides supporting palladium include, for example, the one comprising Pd supported on the perovskite-like composite oxide represented by general formula (10) given below:

$$ABO_3 \tag{10}$$

(In the formula, A represents at least one element selected from the group consisting of rare-earth elements and alkaline-earth metals, and B represents at least one element selected from the group consisting of transition elements except for rare-earth elements and Pd; and Al.)

In the general formula (10), the same as the above-listed rare-earth elements and alkaline-earth metals represented by A and the above-listed transition elements except for rare-earth elements and Pd; and Al represented by B are used.

This perovskite-like composite oxide can be produced by any proper method for preparing the composite oxide, such as the coprecipitation method, the citrate complex method, and the alkoxide method, according as the method mentioned above. In the alkoxide method, the perovskite-like composite oxide can be produced on hydrolysis by adding water into the alkoxide mixed solution.

Palladium can be supported on the perovskite-like composite oxide obtained by any known method, without being limited to any particular method. For example, palladium can be supported on the perovskite-like composite oxide by the method that a salt solution comprising palladium is prepared and then the perovskite-like composite oxide is impregnated with the salt solution and thereafter baked. An amount of palladium supported on the perovskite-like composite oxide is, for example, not more than 20 parts by weight, or preferably 0.5-5 parts by weight, per 100 parts by weight of perovskite-like composite oxide.

Of the perovskite-like composite oxides listed above, the perovskite-like composite oxide containing palladium as a component of the composition is preferably used as the catalyst for synthesis reaction of the present invention.

Further, the perovskite-like composite oxides containing palladium as a component of the composition given by general formulas (5) and (6) given below, especially general formula (6), is further preferably used.

$$A_{1-y}A'_yB_{1-x}Pd_xO_3 \tag{5}$$

(In the formula, A represents at least one element selected from rare-earth elements, A' represents at least one element selected from alkaline-earth metals, B represents at least one element selected from the group consisting of transition elements except for rare-earth elements and Pd; and Al, x represents an atomic rate of Pd, and y represents an atomic rate of $0 \leq y \leq 0.5$.)

$$AB_{1-x}Pd_xO_3 \tag{6}$$

(In the formula, A represents at least one element selected from the group consisting of Y, La, Ce, Pr and Nd, B represents at least one element selected from the group consisting of Mn, Fe, Co and Al, and x represents an atomic rate of Pd.)

The perovskite-like composite oxides containing palladium as the composition include, specifically, for example $La_{1.00}Fe_{0.57}Co_{0.38}Pd_{0.05}O_3$, $La_{0.9}Ce_{0.1}Fe_{0.57}Co_{0.38}Pd_{0.05}O_3$, $La_{1.00}Fe_{0.95}Pd_{0.05}O_3$, $La_{1.00}Co_{0.95}Pd_{0.05}O_3$, $La_{0.9}Ce_{0.1}Al_{0.95}Pd_{0.05}O_3$, $La_{1.00}Fe_{0.57}Mn_{0.38}Pd_{0.05}O_3$, and $La_{1.00}Mn_{0.95}Pd_{0.05}O_3$.

The catalyst for synthesis reaction of the present invention is used for the reaction between a compound indicated in a general formula (1) given below, and a compound indicated in a general formula (2) given below or a compound indicated in a general formula (3) given below.

$$R_1-X \tag{1}$$

(In the formula, $R_1$ represents an aryl group that may have a substituent, a heterocyclic group that may have a substituent, or an alkenyl group that may have a substituent, and X represents a halogen atom, a trifluoromethane sulfonyloxy group, a p-toluenesulfonyloxy group, or a methanesulfonyloxy group.)

$$R_2\text{-M} \quad (2)$$

(In the formula, $R_2$ represents an aryl group that may have a substituent, a heterocyclic group that may have a substituent, or an alkenyl group that may have a substituent, M represents a —B(ORa)$_2$ group or a —Sn(Rb)$_3$ group, Ra represents a hydrogen atom or an alkyl group that may have a substituent, and Rb represents an alkyl group. As a substitute for Ra, an arylene group that may have a substituent or an alkylene group that may have a substituent may be used as a bonding hand of —OBO—, to form a ring including the —OBO—.)

$$R_3HC=CR_4R_5 \quad (3)$$

(In the formula, $R_3$, $R_4$, and $R_5$ each represent a hydrogen atom, an alkyl group that may have a substituent, an aryl group that may have a substituent, a carboxylic acid derivative, an acid amide derivative, or a cyano group.)

Aryl groups of the aryl groups that may have the substituents represented by $R_1$ of the general formula (1), $R_2$ of the general formula (2), and $R_3$, $R_4$ and $R_5$ of the general formula (3) respectively include, for example, aryl groups with carbon numbers between 6 and 14, such as phenyl, tolyl, xylyl, biphenyl, naphthyl, anthryl, phenanthryl, and azulenyl.

No particular limitation is imposed on the substituents of the aryl groups. The substituents suitable for intended purposes and applications can be used, including a hydrocarbon radical and a heteroatom-containing hydrocarbon radical. Examples are alkyl groups with carbon numbers between 1 and 4 such as, for example, methyl, ethyl, propyl, isopropyl, butyl, isobutyl, sec-butyl and tert-butyl; allenyl groups with carbon numbers between 2 and 4 such as, for example, vinyl, 1-methylvinyl, 1-propenyl and allyl; alkynyl groups with carbon numbers between 2 and 4 such as, for example, ethynyl, 1-propynyl and 1-propargyl; cycloalkyl groups with carbon numbers between 3 and 6 such as, for example, cyclopropyl, cyclobutyl, cyclopentyl and cyclohexyl; cycloalkenyl groups with carbon numbers between 5 and 7 such as, for example, cyclopentenyl and cyclohexenyl; aralkyl groups with carbon numbers between 7 and 11 such as, for example, benzyl, α-methylbenzyl and phenethyl; phenyl groups; alkoxy groups with carbon numbers between 1 and 6 such as, for example, methoxy, ethoxy, propoxy, iso-propoxy, n-butoxy, iso-butoxy, sec-butoxy and tert-butoxy; phenoxy groups; alkanoyl groups with carbon numbers between 1 and 6 such as, for example, formyl, acetyl, propionyl, n-butyryl and iso-butyryl; benzoyl groups; alkanoyloxy groups with carbon numbers between 1 and 6 such as, for example, formyloxy, acetyloxy, propionyloxy, n-butyryloxy and iso-butyryloxy; benzoyloxy groups; carboxyl groups; alkoxycarbonyl groups with carbon numbers between 2 and 7 such as, for example, methoxycarbonyl, ethoxycarbonyl, n-propoxycarbonyl, iso-propoxycarbonyl, n-butoxycarbonyl, isobutoxycarbonyl and tert-butoxycarbonyl; carbamoyl groups; N-mono-C$_{1-4}$alkyl-carbamoyl groups such as, for example, N-methylcarbamoyl, N-ethylcarbamoyl, N-propylcarbamoyl, N-isopropylcarbamoyl and N-butylcarbamoyl; N,N-di-C$_{1-4}$alkylcarbamoyl groups such as, for example, N,N-dimethylcarbamoyl, N,N-diethylcarbamoyl, N,N-dipropylcarbamoyl and N,N-dibutylcarbamoyl; cyclic aminocarbonyls such as, for example, 1-athyridinylcarbonyl, 1-azetidinylcarbonyl, 1-pyrrolidinyl-carbonyl, 1-piperidinylcarbonyl, N-methylpiperazinylcarbonyl and morpholinocarbonyl; halogen atoms such as, for example, fluorine, chlorine, bromine and iodine, mono-, di-, or tri-halogeno-C$_{1-4}$alkyl groups such as, for example, chloromethyl, dichloromethyl, trifluoromethyl and trifluoroethyl; oxo groups; amidino groups; imino groups; amino groups; mono-C14alkylamino groups such as, for example, methylamino, ethylamino, propylamino, isopropylamino and butylamino, di-C$_{1-4}$alkyl amino groups such as, for example, dimethylamino, diethylamino, dipropylamino, diisopropylamino and dibutylamino; cyclic amino groups with three to six members that may include one to three hetero atom(s) selected from the group of an oxygen atom, a sulfur atom, a nitrogen atom, etc, in addition to at least one nitrogen atom and carbon atoms such as, for example, athyridinyl, azetidinyl, pyrrolidinyl, pyrrolinyl, pyrrolyl, imidazolyl, pyrazolyl, imidazolidinyl, piperidino, morpholino, dihydropyridyl, pyridyl, N-methylpiperazinyl and N-ethylpiperazinyl group; alkanoylamide groups with carbon numbers between 1 and 6 such as, for example, formamide, acetamide, trifluoroacetamide, propionylamide, butyrylamide and isobutyrylamide; benzamide groups; and carbamoylamino groups; N-C$_{1-4}$alkylcarbamoylamino groups such as, for example, N-methylcarbamoylamino, N-ethylcarbamoylamino, N-propylcarbamoylamino, N-isopropylcarbamoylamino and N-butylcarbamoylamino; N,N-di-C$_{1-4}$alkylcarbamoylamino groups such as, for example, N,N-dimethylcarbamoylamino, N,N-diethylcarbamoyl amino, N,N-dipropylcarbamoylamino and N,N-dibutylcarbamoylamino; alkylene dioxide groups with carbon numbers between 1 and 3 such as, for example, methylenedioxy and ethylenedioxy group; hydroxy groups; epoxy groups (—O—); nitro groups; cyano groups; mercapto groups; sulfo groups; sulfino groups; phosphono groups; sulfamoyl groups, monoalkylsulfamoyl groups with carbon numbers between 1 and 6 such as, for example, N-methylsulfamoyl, N-ethylsulfamoyl, N-propylsulfamoyl, N-isopropylsulfamoyl and N-butylsulfamoyl; di-C$_{1-4}$alylsulfamoyl groups such as, for example, N,N-dimethylsulfamoyl, N,N-diethylsulfamoyl, N,N-dipropylsulfamoyl and N,N-dibutylsulfamoyl, alkylthio groups with carbon numbers between 1 and 6 such as, for example, metylthio, ethylthio, propylthio, isopropylthio, n-butylthio, sec-butylthio and tert-butylthio group; phenylthio groups; alkylsulfinyl groups with carbon numbers between 1 and 6 such as, for example, methylsulfinyl, ethylsulfinyl, propylsulfinyl and butylsulfinyl; phenylsulfinyl groups; alkylsulfonyl groups with carbon numbers between 1 and 6 such as, for example, methylsulfonyl, ethylsulfonyl, propylsulfonyl and butylsulfonyl; and phynylsulfonyl groups. The above mentioned groups may be substituted by one to five substituents listed above.

Heterocyclic groups of the heterocyclic groups that may have substituents, which are represented by $R_1$ of the general formula (1) and $R_2$ of the general formula (2), include for example, five-member rings including one to four hetero atom(s) selected from the group of an oxygen atom, a sulfur atom, a nitrogen atom, etc, in addition to carbon atoms such as, for example, 2- or 3-thienyl, 2- or 3-furyl, 2- or 3-pyronyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, and 1H- or 2H-tetrazolyl; six-member rings including one to four hetero atom(s) selected from the group of an oxygen atom, a sulfur atom, a nitrogen atom, etc, in addition to carbon atoms such as, for example, N-oxido-2-, 3- or 4-pyridyl, 2-, 4- or 5-pyrimidinyl, N-oxide-2-, 4- or 5-pyrimidinyl, thiomorpholinyl, morpholinyl, oxoimidazinyl, dioxotriadinyl, pyrrolidinyl, piperidinyl, pyranyl, thiopyranyl, 1,4-oxadinyl, 1,4-thiazinyl, 1,3-thiazinyl, piperazinyl, triazinyl, oxotriazinyl, 3- or 4-pyridazinyl, and pyrazinyl, N-oxide-3- or 4-pyridazinyl; and five- to eight-member rings or condensed rings thereof, including one to four hetero atom(s) such as, for example, an oxygen atom, a sulfur atom and a nitrogen atom, in addition to carbon atoms such as bicyclic or tricyclic condensed ring groups including one to four hetero atom(s) selected from the group of the oxygen atom, the sulfur atom, the nitrogen atom, etc, in addition to carbon atoms such as, for example, benzofuryl, benzothiazolyl, benzoxazolyl, tetrazolo [1,5-b ] pyridazinyl, triazolo [4,5-b ] pyridazinyl, benzoimidazolyl, quinolyl, iso-quinolyl, cinnolinyl, phthalazinyl, quinazolinyl, quinoxali-nyl, indolizinyl, quinolizinyl, 1,8-naphthylidinyl, prinyl, pte-ridinyl, dibenzofuranyl, carbazolyl, acrydinyl, phenanthridinyl, chromanyl, benzoxadinyl, phenazinyl, phe-nothiazinyl and phenoxadinyl.

No particular limitation is imposed on the substituents of the heterocyclic groups. The substituents suitable for intended purposes and applications can be used, including a hydrocarbon radical and a heteroatom-containing hydrocarbon radical. For example, the same as those listed above can be cited as substituents of the heterocyclic groups. The above mentioned groups may be substituted by one to five substituents listed above.

Alkenyl groups of the alkenyl groups that may have substituents, which are represented by $R_1$ of the general formula (1) and $R_2$ of the general formula (2), include for example, alkenyl groups with carbon numbers between 2 and 18, such as vinyl, allyl, methallyl, isopropenyl, 1-propenyl, 2-prope-nyl, 2-methyl-1-propenyl, butenyl, pentenyl, hexenyl, hepty-nyl, octenyl, nonenyl, decenyl, undecenyl, dodecenyl, tet-radecenyl, hexadecenyl and octadecenyl.

No particular limitation is imposed on the substituents of the alkenyl groups. The substituents suitable for intended purposes and applications can be used, including a hydrocarbon radical and a heteroatom-containing hydrocarbon radical. For example, the same as those listed above can be cited as substituents of the alkenyl groups. The above mentioned groups may be substituted by one to five substituents listed above.

Alkyl groups of the alkyl groups that may have the substituents indicated by Ra of the general formula (2), the alkyl group indicated by Rb of the general formula (2), and alkyl groups of the alkyl groups that may have the substituents indicated by $R_3$, $R_4$ and $R_5$ of the general formula (3) include, for example, alkyl groups with carbon numbers between 1 and 18, such as methyl, ethyl, propyl, iso-propyl, n-butyl, iso-butyl, sec-butyl and tert-butyl, pentyl, iso-pentyl, sec-pentyl, hexyl, heptyl, n-octyl, isooctyl, 2-ethylhexyl, nonyl, decyl, isodecyl, dodecyl, tetradecyl, hexadecyl, and octade-cyl.

No particular limitation is imposed on the substituents of the alkyl groups. The substituents suitable for intended purposes and applications can be used, including a hydrocarbon radical and a heteroatom-containing hydrocarbon radical. For example, the same as those listed above can be cited as substituents of the alkyl groups. The above mentioned groups may be substituted by one to five substituents listed above.

The arylene groups that may have a substituent in the general formula (2), which is used as a substitute for Ra and is used as a bonding hand of —OBO— to form a ring including —OBO—, include, for example, arylene groups with carbon numbers between 6 and 10, such as phenylene, tolylene, xylylene, and naphthylene.

No particular limitation is imposed on the substituents of the arylene groups. The substituents suitable for intended purposes and applications can be used, including a hydrocarbon radical and a heteroatom-containing hydrocarbon radical. For example, the same as those listed above can be cited as substituents of the arylene groups. The above mentioned groups may be substituted by one to five substituents listed above.

Alkylene groups of the alkylene groups that may have substituents in the general formula (2), which is used as a substitute for Ra and is used as a bonding hand of —OBO— to form a ring including —OBO—, include, for example, alkylene groups with carbon numbers between 1 and 18, such as methylene, ethylene, propylene, iso-propylene, n-buty-lene, iso-butylene, sec-butylene, tert-butylene, pentylene, iso-pentylene, sec-pentylene, hexylene, heptylene, octylene, 2-ethylhexylene, nonylene, decylene, isodecylene, dode-cylene, tetradecylene, hexadecylene, and octadecylene.

No particular limitation is imposed on the substituents of the alkylene groups. The substituents suitable for intended purposes and applications can be used, including a hydrocarbon radical and a heteroatom-containing hydrocarbon radical. For example, the same as those listed above can be cited as substituents of the alkylene groups. The above mentioned groups may be substituted by one to five substituents listed above.

In the case where as a substitute for Ra, the above-said arylene group or the above-said alkylene group is used as a bonding hand of —OBO—, to form a ring including —OBO—, the following general formula (11) is used in place of the general formula (2) above.

(11)

(In the formula, $R_2$ represents an aryl group that may have a substituent, a heterocyclic group that may have a substituent, or an alkenyl group that may have a substituent, and Ra represents an arylene group that may have a substituent or an alkylene group that may have a substituent.)

To be more specific, when the arylene group that may have a substituent is phenylene, for example, the following general formula (12) is used. On the other hand, when the alkylene group that may have a substituent is 1,1,2,2,-tetramethyleth-ylene, for example, the following general formula (13) is used.

(12)

(13)

The halogen atoms indicated by X of the general formula (1) include, for example, chlorine, bromine and iodine.

The carboxylic acid derivatives indicated by R3, R4, and R5 of the general formula (3) include, for example, alkoxy-carbonyl groups, such as methoxycarbonyl (—COOMe), ethoxycarbonyl (—COOEt), and t-butoxycarbonyl (—COOtBu).

More concrete examples of the compounds of these carboxylic acid derivatives in the general formula (3) are shown in TABLE 1.

TABLE 1

| R3 | R4 | R5 | Compound name | Structural formula |
|---|---|---|---|---|
| H | H | $CO_2tBu$ | Tert-butyl-acrylate | $H_2C\!=\!CHCOOtBu$ |
| H | H | $CO_2Me$ | Methyl acrylate | $H_2C\!=\!CHCOOMe$ |
| H | H | $CO_2Et$ | Ethyl acrylate | $H_2C\!=\!CHCOOEt$ |
| Me | H | $CO_2Et$ | Ethyl crotonate | $MeCH\!=\!CHCOOEt$ |
| Me | Me | $CO_2Et$ | Ethyl tiglicate | $MeCH\!=\!C(Me)COOEt$ |
| H | Me | $CO_2Et$ | Ethyl methacrylate | $H_2C\!=\!C(Me)COOEt$ |

The acid amide derivatives indicated by R3, R4 and R5 of the general formula (3) include, for example, N-mono- or N,N-dialkylcarbamoyl group, such as a carbamoyl (—$CONH_2$) group and, for example, N-methylcarbomoyl (—CONHMe) group and N,N-dimethylcarbamoyl (—$CONH(Me)_2$).

More concrete examples of the compounds of these acid amide derivatives in the general formula (3) are shown in TABLE 2.

TABLE 2

| R3 | R4 | R5 | Compound name | Structural formula |
|---|---|---|---|---|
| H | H | $CONH_2$ | Acrylamide | $H_2C\!=\!CHCNH_2$ |
| H | H | CONHMe | N-methylacryluaminde | $H_2C\!=\!CHCONHMe$ |
| H | H | $CONMe_2$ | N,N-dimethylacrylamide | $H_2C\!=\!CHCONMe_2$ |
| Me | H | CONHMe | N-methylcrotonateamide | $MeCH\!=\!CHCONHMe$ |
| Me | Me | CONHMe | N-methyltiglicateamide | $MeCH\!=\!C(Me)CONHMe$ |
| H | Me | CONHMe | N-methylmethacrylateamide | $H_2C\!=\!C(Me)CONHMe$ |

More concrete examples of the compounds of the cyano groups indicated by R3, R4 and R5 in the general formula (3) are shown in TABLE 3.

TABLE 3

| R3 | R4 | R5 | Compound name | Structural formula |
|---|---|---|---|---|
| H | H | CN | Acrylonitrile | $N_2C\!=\!CHCN$ |
| Me | H | CN | Crotononitrile | $MeCH\!=\!CHCN$ |
| H | Me | CN | Methacrylonitrile | $H_2C\!=\!C(Me)CN$ |

When a compound in the general formula (1) and a compound in the general formula (2) are allowed to react with each other, a compound in the following general formula (14) is produced.

$$R_1\text{—}R_2 \quad (14)$$

(In the formula, $R_1$ and $R_2$ indicate an aryl group that may have a substituent, a heterocyclic group that may have a substituent, or an alkenyl group that may have a substituent.)

It should be noted that the aryl group that may have a substituent, the heterocyclic group that may have a substituent, or the alkenyl group that may have a substituent as are indicated by $R_1$ and $R_2$ in the general formula (14) are synonyms of the above.

Where M of the general formula (2) is —B(ORa)2in the reaction of the compound in the general formula (1) and the compound in the general formula (2), the synthesizing method for compound of the present invention is given by the following reaction formula (15) named the Suzuki Cross-couplings.

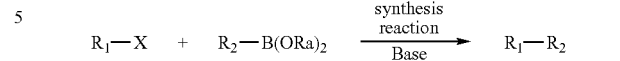

Where M of the general formula (2) is —$Sn(Rb)_3$ in the reaction of the compound in the general formula (1) and the compound in the general formula (2), the synthesizing method for compound of the present invention is given by the following reaction formula (16) named the Stille Cross-couplings.

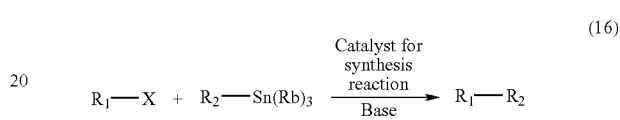

When the compound in the general formula (1) and the compound in the general formula (3) are allowed to react with each other, a compound in the following general formula (17) is produced.

$$R_1R_3C\!=\!CR_5R_4 \quad (17)$$

(In the formula, $R_1$ indicates an aryl group that may have a substituent, a heterocyclic group that may have a substituent, or an alkenyl group that may have a substituent, and $R_3$, $R_4$ and $R_5$ each represent a hydrogen atom or an alkyl group that may have a substituent, an aryl group that may have a substituent, a carboxylic acid derivative, an acid amide derivative, or a cyano group.)

It should be noted that the aryl group that may have a substituent, the heterocyclic group that may have a substituent, or the alkenyl group that may have a substituent as are indicated by $R_1$ in the general formula (17), and the hydrogen atom, the alkyl group that may have a substituent, the aryl group that may have a substituent, the carboxylic acid derivative, the acid amide derivative, or the cyano group as are indicated by $R_3$, $R_4$ and $R_5$ in the general formula (17) are synonyms of the above.

In the synthesizing method for compound of the present invention, the reaction of the compound in the general formula (1) and the compound in the general formula (3) is given by the following reaction formula (18) named the Heck Cross-couplings.

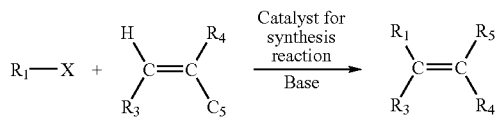

(18)

In the reaction formulas (15), (16) and (18), the compound in the general formula (1) is allowed to react with the compound in the general formula (2) or the compound in the general formula (3) in the presence of the base and the perovskite-like composite oxide comprising palladium which is the catalyst for synthesis reaction of the present invention.

The bases that may be used in this reaction include, for example, hydroxides such as sodium hydroxide and potassium hydroxide, inorganic salts including carbonates, such as sodium carbonate ($Na_2CO_3$), potassium carbonate ($K_2CO_3$) and cesium carbonate ($Cs_2CO_3$), and phosphates, such as sodium phosphate ($Na_3PO_4$) and potassium phosphate ($K_3PO_4$), and organic salts such as triethylamines, pyridine, morpholine, quinoline, piperidine, DBU (diazabicycloundecene) and anilines. These bases may be used alone or in combination of two or more.

Although no particular limitation is imposed on the proportion in which the compound in the general formula (1), and the compound in the general formula (2) or the compound in the general formula (3) are mixed in this reaction, those compounds are mixed in the proportion of e.g. 0.1-10 equivalents, or preferably 0.5-2 equivalents, of the compound in the general formula (2) or the compound in the general formula (3) per the compound in the general formula (1).

Although no particular limitation is imposed on the proportion in which the perovskite-like composite oxide comprising palladium is added in this reaction. A content of palladium contained in the perovskite-like composite oxide added is in the range of e.g. 0.001-10 mole-percent, or preferably 0.001-5 mole-percent.

Although no particular limitation is imposed on the base in this reaction, for example 1-30 equivalents, or preferably 1-10 equivalents, of the base is added.

In this reaction, for example, reaction pressure ranges from 0 to 5,000 KPa, or preferably from 0 to 3,000 KPa, reaction temperature ranges from 0 to 250° C., or preferably from 0 to 150° C., and reaction time ranges from 0.1 hr. to 72 hrs., or preferably from 0.5 hr. to 24 hrs.

In this reaction, reaction solvent may be used. The reaction solvents that may be used include, for example, water and aqueous solvents including alcohols such as methanol, ethanol and isopropanol (IPA). These reaction solvents may be used alone or in combination of two or more.

Also, in this reaction, an additive for accelerating the reaction may be added. Those additives include, for example, organic ammonium halide such as tetra-n-butylammoniumbromide (TBAB). For example 1-200 mole-percent additive is added.

To be more specific, for example, the compound in the general formula (1), and the compound in the general formula (2) or the compound in the general formula (3) together with the perovskite-like composite oxide comprising palladium and the base are added into the reaction solvent in the proportion specified above and are allowed to react with each other under the reaction conditions recited above. From this reaction, the compound shown in the general formula (14) or the compound shown in the general formula (17) can be obtained.

In the synthesizing method for compound of the present invention, the compound in the general formula (14) or the compound in the general formula (17) can be synthesized at an improved yield by using the Suzuki cross-couplings, the Stille cross-couplings, or the Heck cross-couplings in the presence of the perovskite-like composite oxide comprising palladium.

Also, in the synthesizing method for compound of the present invention, the perovskite-like composite oxide comprising palladium is in the solid state after completion of the reaction and thus can be easily collected from a reaction mixed solution by filtration or decantation. Besides, the perovskite-like composite oxide comprising palladium thus collected can be recycled with no significant reduction in catalytic activity of this reaction. Accordingly, the costs involved in the disposal of the catalyst for synthesis reaction can be cut and, as a result, the manufacturing costs can be reduced.

Thus, the synthesizing method for compound of the present invention can be used effectively, for example, in the applications in which the Suzuki cross-couplings can be used industrially, such as the synthesis of medical products having a biphenyl skeleton as shown below.

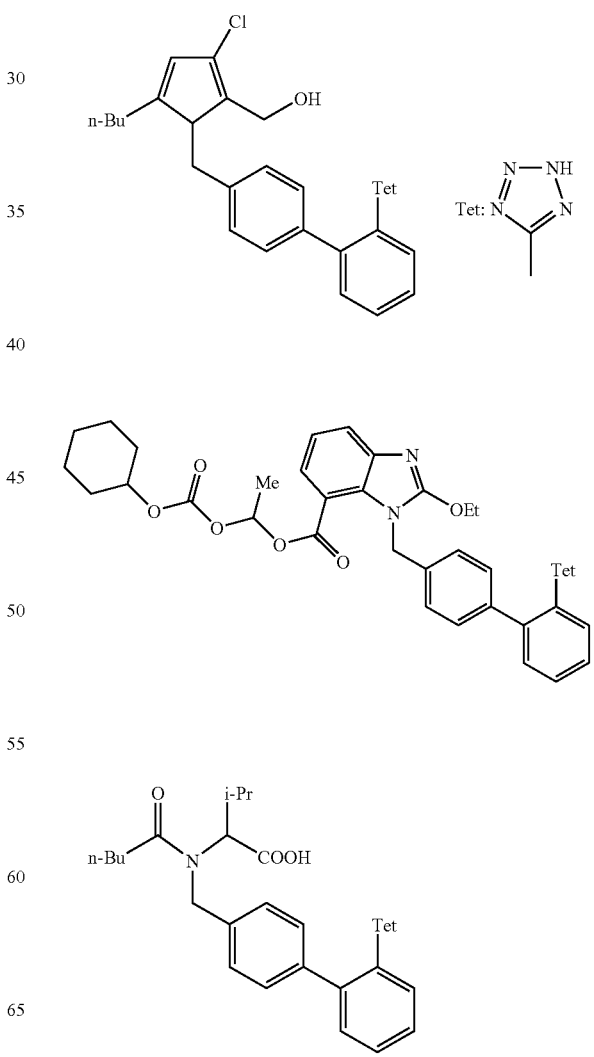

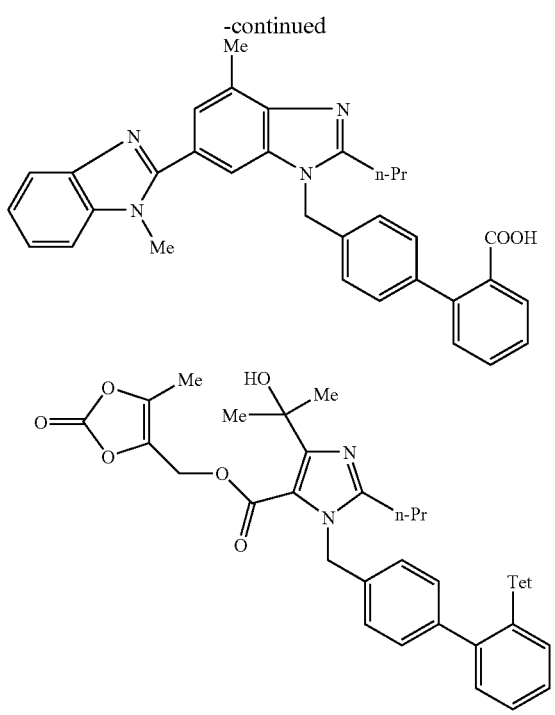

EXAMPLES

While in the following, the present invention will be described in further detail with reference to Examples of production and Examples of synthesis, the present invention is not limited to any of them.

1) Examples of Production of Catalyst for Synthesis Reaction (Perovskite-like Composite Oxide):

Example of Production 1 (Production of $La_{1.00}Fe_{0.57}Co_{0.38}Pd_{0.05}O_3$)

| | |
|---|---|
| Lanthanum ethoxyethylate | 40.6 g (0.100 mol), |
| Iron ethoxyethylate | 18.4 g (0.057 mol), and |
| Cobalt ethoxyethylate | 9.0 g (0.038 mol) | were added into a 500 ml round-bottomed flask and then 200 ml of toluene was poured and mixed with stirring, to prepare an alkoxide mixed solution. Then, 1.52 g (0.005 mol) of palladium acethylacetonate was dissolved in 100 ml of toluence. The resultant solution was further poured into the alkoxide mixed solution in the round-bottomed flask, to prepare a homogeneous mixed solution containing LaFeCoPd.

Then, 200 ml of demineralized water was dropped in the round-bottomed flask for about fifteen minutes. As a result, a brown viscous precipitate was produced on hydrolysis.

Then, after the precipitate thus produced was stirred at room temperature for two hours, the toluene and water were removed therefrom by evaporation under reduced pressure, to obtain a precursor of the LaFeCoPd composite oxide. Sequentially, this precursor was placed on a petri dish and then was dried by circulation drying at 60° C. for twenty-four hours. Thereafter, it was heat-treated at 800° C. for one hour in the atmosphere using an electric furnace, to obtain blackish brown fine particles.

The X-ray diffraction measurement of the fine particles obtained was made. From this measurement, the fine particles were identified as a single crystalline phase of composite oxide having a perovskite-like structure of $La_{1.00}Fe_{0.57}Co_{0.38}Pd_{0.05}O_3$. Also, it was found that they had a specific surface of 24 $m^2/g$ and that a Pd content in the composite oxide was 2.16 mass %.

Example of Production 2 (Production of $La_{0.9}Ce_{0.1}Fe_{0.57}Co_{0.38}Pd_{0.05}O_3$)

| | |
|---|---|
| Lanthanum methoxypropylate | 36.6 g (0.090 mol), |
| Cerium methoxypropylate | 4.1 g (0.010 mol), |
| Iron methoxypropylate | 18.4 g (0.057 mol), and |
| Cobalt methoxypropylate | 9.0 g (0.038 mol) | were added into a 500 ml round-bottomed flask and then 200 ml of toluene was poured and mixed with stirring, to prepare an alkoxide mixed solution. Then, 1.52 g (0.005 mol) of palladium acethylacetonate was dissolved in 200 ml of toluence. The resultant solution was further poured into the alkoxide mixed solution in the round-bottomed flask, to prepare a homogeneous mixed solution containing LaCeFeCoPd.

Then, 200 ml of demineralized water was dropped in the round-bottomed flask for about fifteen minutes. As a result, a brown viscous precipitate was produced on hydrolysis.

Then, after the precipitate thus produced was stirred at room temperature for two hours, the toluene and water were removed therefrom by evaporation under reduced pressure, to obtain a precursor of the LaCeFeCoPd composite oxide. Sequentially, this precursor was placed on a petri dish and then was dried by circulation drying at 60° C. for twenty-four hours. Thereafter, it was heat-treated at 600° C. for one hour in the atmosphere using the electric furnace, to obtain blackish brown fine particles.

The X-ray diffraction measurement of the fine particles obtained was made. From this measurement, the fine particles were identified as a single crystalline phase of composite oxide having a perovskite-like structure of $La_{0.9}Ce_{0.1}Fe_{0.57}Co_{0.38}Pd_{0.05}O_3$. Also, it was found that they had a specific surface of 37 $m^2/g$ and that a Pd content in the composite oxide was 2.16 mass %.

Example of Production 3 (Production of $La_{1.00}Fe_{0.95}Pd_{0.05}O_3$)

| | |
|---|---|
| Lanthanum $^i$ propoxyethylate | 44.9 g (0.100 mol), and |
| Iron $^i$ propoxyethylate | 34.7 g (0.095 mol), | were added into a 500 ml round-bottomed flask and then 200 ml of toluene was poured and mixed with stirring, to prepare an alkoxide mixed solution. Then, 1.52 g (0.005 mol) of palladium acethylacetonate was dissolved in 100 ml of toluence. The resultant solution was further poured into the alkoxide mixed solution in the round-bottomed flask, to prepare a homogeneous mixed solution containing LaFePd.

Then, 200 ml of demineralized water was dropped in the round-bottomed flask for about fifteen minutes. As a result, a brown viscous precipitate was produced on hydrolysis.

Then, after the precipitate thus produced was stirred at room temperature for two hours, the toluene and water were removed therefrom by evaporation under reduced pressure, to obtain a precursor of the LaFePd composite oxide. Sequentially, this precursor was placed on a petri dish and then was dried by circulation drying at 60° C. for twenty-four hours. Thereafter, it was heat-treated at 800° C. for one hour in the atmosphere using the electric furnace, to obtain blackish brown fine particles.

The X-ray diffraction measurement of the fine particles obtained was made. From this measurement, the fine particles were identified as a single crystalline phase of composite oxide having a perovskite-like structure of $La_{1.00}Fe_{0.95}Pd_{0.05}O_3$. Also, it was found that they had a specific surface of 8.1 m$^2$/g and that a Pd content in the composite oxide was 2.17 mass %.

Example of Production 4 (Production of $La_{1.00}Co_{0.95}Pd_{0.05}O_3$)

| Lanthanum methoxyethylate | 36.4 g (0.100 mol), and |
| Cobalt methoxyethylate | 19.9 g (0.095 mol) | were added into a 500 ml round-bottomed flask and then 200 ml of toluene was poured and mixed with stirring, to prepare an alkoxide mixed solution. Then, 1.52 g (0.005 mol) of palladium acethylacetonate was dissolved in 100 ml of toluene. The resultant solution was further poured into the alkoxide mixed solution in the round-bottomed flask, to prepare a homogeneous mixed solution containing LaCoPd.

Then, 200 ml of demineralized water was dropped in the round-bottomed flask for about fifteen minutes. As a result, a brown viscous precipitate was produced on hydrolysis.

Then, after the precipitate thus produced was stirred at room temperature for two hours, the toluene and water were removed therefrom by evaporation under reduced pressure, to obtain a precursor of the LaCoPd composite oxide. Sequentially, this precursor was placed on a petri dish and then was dried by circulation drying at 60° C. for twenty-four hours. Thereafter, it was heat-treated at 800° C. for one hour in the atmosphere using the electric furnace, to obtain blackish brown fine particles.

The X-ray diffraction measurement of the fine particles obtained was made. From this measurement, the fine particles were identified as a single crystalline phase of composite oxide having a perovskite-like structure of $La_{1.00}Co_{0.95}Pd_{0.05}O_3$. Also, it was found that they had a specific surface of 4.8 m$^2$/g and that a Pd content in the composite oxide was 2.15 mass %.

Example of Production 5 (Production of $La_{0.9}Ce_{0.1}Al_{0.95}Pd_{0.05}O_3$)

| Lanthanum $^n$ butoxide | 32.2 g (0.090 mol), |
| Cerium $^n$ butoxide | 3.6 g (0.010 mol), and |
| Aluminum $^n$ butoxide | 23.4 g (0.095 mol) | were added into a 500 ml round-bottomed flask and then 200 ml of toluene was poured and mixed with stirring, to prepare an alkoxide mixed solution. Then, 1.52 g (0.005 mol) of palladium acethylacetonate was dissolved in 100 ml of toluence. The resultant solution was further poured into the alkoxide mixed solution in the round-bottomed flask, to prepare a homogeneous mixed solution containing LaCeAlPd.

Then, 200 ml of demineralized water was dropped in the round-bottomed flask for about fifteen minutes. As a result, a brown viscous precipitate Was produced on hydrolysis.

Then, after the precipitate thus produced was stirred at room temperature for two hours, the toluene and water were removed therefrom by evaporation under reduced pressure, to obtain a precursor of the LaCeAlPd composite oxide. Sequentially, this precursor was placed on a petri dish and then was dried by circulation drying at 60° C. for twenty-four hours. Thereafter, it was heat-treated at 900° C. for one hour in the atmosphere using the electric furnace, to obtain blackish brown fine particles.

The X-ray diffraction measurement of the fine particles obtained was made. From this measurement, the fine particles were identified as a single crystalline phase of composite oxide having a perovskite-like structure of $La_{0.9}Ce_{0.1}Al_{0.95}Pd_{0.05}O_3$. Also, it was found that they had a specific surface of 7.2 m$^2$/g and that a Pd content in the composite oxide was 2.44 mass %.

Example of Production 6 (Production of $La_{1.00}Fe_{0.57}Mn_{0.38}Pd_{0.05}O_3$)

| Lanthanum ethoxypropylate | 44.9 g (0.100 mol), |
| Iron ethoxypropylate | 20.8 g (0.057 mol), and |
| Manganese ethoxypropylate | 9.9 g (0.038 mol) | were added into a 500 ml round-bottomed flask and then 200 ml of toluene was poured and mixed with stirring, to prepare an alkoxide mixed solution. Then, 2.37 g (0.005 mol) of bis(2,2,6,6-tetramethyl-3,5-heptanedionate) palladium was dissolved in 100 ml of toluence. The resultant solution was further poured into the alkoxide mixed solution in the round-bottomed flask, to prepare a homogeneous mixed solution containing LaFeMnPd.

Then, 200 ml of demineralized water was dropped in the round-bottomed flask for about fifteen minutes. As a result, a brown viscous precipitate was produced on hydrolysis.

Then, after the precipitate thus produced was stirred at room temperature for two hours, the toluene and water were removed therefrom by evaporation under reduced pressure, to obtain a precursor of the LaFeMnPd composite oxide. Sequentially, this precursor was placed on a petri dish and then was dried by circulation drying at 60° C. for twenty-four hours. Thereafter, it was heat-treated at 700° C. for one hour in the atmosphere using the electric furnace, to obtain blackish brown fine particles.

The X-ray diffraction measurement of the fine particles obtained was made. From this measurement, the fine particles were identified as a single crystalline phase of composite oxide having a perovskite-like structure of $La_{1.00}Fe_{0.57}Mn_{0.38}Pd_{0.05}O_3$. Also, it was found that they had a specific surface of 14 m$^2$/g and that a Pd content in the composite oxide was 2.17 mass %.

Example of Production 7 (Production of $La_{1.00}Mn_{0.95}Pd_{0.05}O_3$)

| Lanthanum $^n$ butoxypropylate | 53.3 g (0.100 mol), and |
| Manganese $^n$ butoxypropylate | 30.1 g (0.095 mol) | were added into a 500 ml round-bottomed flask and then 200 ml of toluene was poured and mixed with stirring, to prepare an alkoxide mixed solution. Then, 2.37 g (0.005 mol) of bis(2,2,6,6-tetramethyl-3,5 heptanedionate) palladium was dissolved in 100 ml of toluence. The resultant solution was further poured into the alkoxide mixed solution in the round-bottomed flask, to prepare a homogeneous mixed solution containing LaMnPd.

Then, 200 ml of demineralized water was dropped in the round-bottomed flask for about fifteen minutes. As a result, a brown viscous precipitate was produced on hydrolysis.

Then, after the precipitate thus produced was stirred at room temperature for two hours, the toluene and water were removed therefrom by evaporation under reduced pressure, to obtain a precursor of the LaMnPd composite oxide. Sequentially, this precursor was placed on a petri dish and then was dried by circulation drying at 60° C. for twenty-four hours. Thereafter, it was heat-treated at 800° C. for one hour in the atmosphere using the electric furnace, to obtain blackish brown fine particles.

The X-ray diffraction measurement of the fine particles obtained was made. From this measurement, the fine particles were identified as a single crystalline phase of composite oxide having a perovskite-like structure of $La_{1.00}Mn_{0.95}Pd_{0.05}O_3$. Also, it was found that they had a specific surface of 20 m²/g and that a Pd content in the composite oxide was 2.17 mass %.

Example of Production 8 (Production of $La_{1.00}Fe_{0.57}Co_{0.38}Pd_{0.05}O_3$)

| | |
|---|---|
| Lanthanum nitrate (La(NO₃)₃.6H₂O) | 43.3 g (0.100 mol), |
| Iron nitrate (Fe(NO₃)₃.9H₂O) | 23.0 g (0.057 mol), |
| Cobalt nitrate (Co(NO₃)₂.3H₂O) | 9.0 g (0.038 mol), and |
| Palladium nitrate aqueous solution (a Pd content of 4.399 mass %) | 12.1 g (equivalent to 0.53 g of Pd equal to 0.005 mol) | were dissolved with stirring in a 500 ml beaker, while pouring 200 ml of demineralized water into it, to prepare a mixed aqueous salt solution containing LaFeCoPd.

Meanwhile, 624 g of ammonium carbonate (a NH₃ content of 30%) was dissolved in 600 ml of demineralized water in a 2L beaker, to prepare a neutralizing agent solution. The mixed aqueous salt solution containing LaFeCoPd as previously prepared was dropped in the neutralizing agent solution with stirring with a stirrer for about fifteen minutes. As a result, a precipitate was produced by the neutralization coprecipitation.

Then, after the precipitate was filtered to remove the water under reduced pressure, the resultant precipitate was placed on a petri dish and then was dried by circulation drying at 60° C. for twenty-four hours. Thereafter, it was heat-treated at 800° C. for three hours in the atmosphere using the electric furnace, to obtain black fine particles.

The X-ray diffraction measurement of the fine particles obtained was made. From this measurement, the fine particles were identified as a single crystalline phase of composite oxide having a perovskite-like structure of $La_{1.00}Fe_{0.57}Co_{0.38}Pd_{0.05}O_3$. Also, it was found that they had a specific surface of 17.4 m²/g and that a Pd content in the composite oxide was 2.16 mass %.

Example of Production 9 (Production of $Nd_{0.90}Y_{0.10}Fe_{0.95}Pd_{0.05}O_3$)

| | |
|---|---|
| Neodymium nitrate (Nd(NO₃)₃.6H₂O) | 39.5 g (0.090 mol), |
| Yttrium nitrate (Y(NO₃)₃.6H₂O) | 3.8 g (0.010 mol), |
| Iron nitrate (Fe(NO₃)₃.9H₂O) | 38.4 g (0.095 mol), and |
| Palladium nitrate aqueous solution (a Pd content of 4.399 mass %) | 12.1 g (equivalent to 0.53 g of Pd equal to 0.005 mol) | were dissolved with stirring in a 1L round-bottomed flask, while pouring 100 ml of purified water into it, to prepare a homogeneous mixed solution containing NdYFePd. Then, after 50.4 g of citric acid (0.24 mol) was dissolved in the purified water, the resultant solution was poured in the homogeneous mixed solution containing NdYFePd, to prepare a citric acid mixed aqueous salt solution containing NdYFePd.

Sequentially, this citric acid mixed aqueous salt solution was dried off by evaporation under reduced pressure within a rotary evaporator as was controlled in temperature using an oil bath of 60-80° C. After passage of about three hours and when the solution came into a starch-syrup-like state, the temperature of the oil bath was gradually raised up to 250° C. and dried under reduced pressure at 250° C. for one hour, to obtain a citrate complex.

The citrate complex thus obtained was heat-treated at 300° C. for three hours in the atmosphere and further pulverized in a mortar. Thereafter, it was heat-treated again at 700° C. for three hours in the atmosphere using the electric furnace, to obtain blackish brown fine particles.

The X-ray diffraction measurement of the fine particles obtained was made. From this measurement, the fine particles were identified as a single crystalline phase of composite oxide having a perovskite-like structure of $Nd_{0.90}Y_{0.10}Fe_{0.95}Pd_{0.05}O_3$. Also, it was found that they had a specific surface of 26.2 m²/g and that a Pd content in the composite oxide was 2.16 mass %.

2) Examples of Synthesis by Suzuki Cross-couplings 2-1) Reaction between arylbromide and boronic Acid The arylbromide and boronic acid shown in TABLE 4 were allowed to react with each other under the reaction conditions shown in TABLE 4, using the Pd-containing perovskite-like composite oxide produced in Example of production 1 as the catalyst for synthesis reaction. Yields in the respective reactions are shown in TABLE 4.

TABLE 4

| | Arylbromide | Boronic acid | Product | Base | Additive | Catalyst for synthesis reaction (mol %) |
|---|---|---|---|---|---|---|
| Example of synthesis 1 | Br—⟨⟩—OMe | ⟨⟩—B(OH)₂ | ⟨⟩—⟨⟩—OMe | K₂CO₃ | / | 0.05 |

TABLE 4-continued

| Example | Aryl halide | Boronic acid | Product | Base | Additive | Catalyst (mol%) |
|---|---|---|---|---|---|---|
| Example of synthesis 2 | 4-bromoanisole | phenylboronic acid | 4-methoxybiphenyl | Cs$_2$CO$_3$ | / | 0.0038 |
| Example of synthesis 3 | 4-bromoanisole | 2-methoxyphenylboronic acid | 2,4'-dimethoxybiphenyl | K$_2$CO$_3$ | / | 0.05 |
| Example of synthesis 4 | 3-bromopyridine | phenylboronic acid | 3-phenylpyridine | K$_2$CO$_3$ | / | 0.05 |
| Example of synthesis 5 | 2-bromoanisole | 2-methoxyphenylboronic acid | 2,2'-dimethoxybiphenyl | K$_2$CO$_3$ | / | 0.05 |
| Example of synthesis 6 | 4-bromobenzotrifluoride | phenylboronic acid | 4-(trifluoromethyl)biphenyl | K$_2$CO$_3$ | / | 0.05 |
| Example of synthesis 7 | 4-bromoanisole | 3,4,5-trimethoxyphenylboronic acid | 3,4,5,4'-tetramethoxybiphenyl | K$_2$CO$_3$ | TBAB (1.1 eq) | 0.05 |
| Example of synthesis 8 | 4-bromoanisole | 3,4,5-trimethoxyphenylboronic acid | 3,4,5,4'-tetramethoxybiphenyl | K$_2$CO$_3$ | / | 0.05 |
| Example of synthesis 9 | 4-bromonitrobenzene | phenylboronic acid | 4-nitrobiphenyl | K$_2$CO$_3$ | TBAB (1.1 eq) | 0.05 |
| Example of synthesis 10 | 4-bromonitrobenzene | phenylboronic acid | 4-nitrobiphenyl | K$_2$CO$_3$ | / | 0.05 |
| Example of synthesis 11 | 4-bromofluorobenzene | phenylboronic acid | 4-fluorobiphenyl | K$_2$CO$_3$ | / | 0.05 |
| Example of synthesis 12 | 4-bromoanisole | 4-(trifluoromethoxy)phenylboronic acid | 4-methoxy-4'-(trifluoromethoxy)biphenyl | K$_2$CO$_3$ | / | 0.05 |
| Example of synthesis 13 | 2-bromobenzonitrile | 4-methylphenylboronic acid | 4'-methyl-2-cyanobiphenyl | K$_2$CO$_3$ | / | 0.05 |

TABLE 4-continued

|  | Time (h) | Yield (%) |
|---|---|---|
| Example of synthesis 1 | 0.5 | 95 |
| Example of synthesis 2 | 39 | 91 |
| Example of synthesis 3 | 0.5 | 95 |
| Example of synthesis 4 | 18 | 85 |
| Example of synthesis 5 | 1 | 89 |
| Example of synthesis 6 | 18 | 92 |
| Example of synthesis 7 | 18 | 93 |
| Example of synthesis 8 | 18 | 60 |
| Example of synthesis 9 | 10 | 95 |
| Example of synthesis 10 | 10 | 92 |
| Example of synthesis 11 | 3 | 91 |
| Example of synthesis 12 | 18 | 95 |
| Example of synthesis 13 | 10 | 91 |

Reaction condition: $LaFe_{0.57}Co_{0.38}Pd_{0.05}O_3$(0.05 mol % Pd), IPA-$H_2O$(1:1, v/v). 80° C., 3 eq. Base, 1.5 eq. Boronic acid
Conversion ratio (Yield) identified by $^1H$ NMR Also, the arylbromide and boronic acid shown in TABLE 5 were allowed to react with each other under the reaction conditions shown in TABLE 5, using the Pd-containing perovskite-like composite oxide produced in Examples of production 2-9 as the catalyst for synthesis reaction. Yields in the respective reactions are shown in TABLE 5.

TABLE 5

| | Arylbromide | Boronic acid | Product | Catalyst | Base |
|---|---|---|---|---|---|
| Example of synthesis 14 | Br—⌬—OMe | ⌬—B(OH)$_2$ | ⌬—⌬—OMe | $La_{0.9}Ce_{0.1}Fe_{0.57}Co_{0.38}Pd_{0.05}O_3$ | $K_2CO_3$ |
| Example of synthesis 15 | Br—⌬—OMe | ⌬—B(OH)$_2$ | ⌬—⌬—OMe | $LaFe_{0.95}Pd_{0.05}O_3$ | $K_2CO_3$ |

TABLE 5-continued

| | | | | Catalyst |  |
|---|---|---|---|---|---|
| Example of synthesis 16 | Br—⟨C6H4⟩—OMe + ⟨C6H5⟩—B(OH)₂ → ⟨C6H4⟩—⟨C6H4⟩—OMe | | | $LaCo_{0.95}Pd_{0.05}O_3$ | $K_2CO_3$ |
| Example of synthesis 17 | Br—⟨C6H4⟩—OMe + ⟨C6H5⟩—B(OH)₂ → ⟨C6H4⟩—⟨C6H4⟩—OMe | | | $La_{0.9}Ce_{0.1}Al_{0.95}Pd_{0.05}O_3$ | $K_2CO_3$ |
| Example of synthesis 18 | Br—⟨C6H4⟩—OMe + ⟨C6H5⟩—B(OH)₂ → ⟨C6H4⟩—⟨C6H4⟩—OMe | | | $LaFe_{0.57}Mn_{0.38}Pd_{0.05}O_3$ | $K_2CO_3$ |
| Example of synthesis 19 | Br—⟨C6H4⟩—OMe + ⟨C6H5⟩—B(OH)₂ → ⟨C6H4⟩—⟨C6H4⟩—OMe | | | $LaMn_{0.95}Pd_{0.05}O_3$ | $K_2CO_3$ |
| Example of synthesis 20 | Br—⟨C6H4⟩—OMe + ⟨C6H5⟩—B(OH)₂ → ⟨C6H4⟩—⟨C6H4⟩—OMe | | | $LaFe_{0.57}Co_{0.38}Pd_{0.05}O_3$ | $K_2CO_3$ |
| Example of synthesis 21 | Br—⟨C6H4⟩—OMe + ⟨C6H5⟩—B(OH)₂ → ⟨C6H4⟩—⟨C6H4⟩—OMe | | | $Nd_{0.90}Y_{0.10}Fe_{0.95}Pd_{0.05}O_3$ | $K_2CO_3$ |

| | Additive | Catalyst for synthesis reaction (mol %) | Time (h) | Yield (%) |
|---|---|---|---|---|
| Example of synthesis 14 | / | 0.05 | 2 | 99.5 |
| Example of synthesis 15 | / | 0.05 | 2 | 98.6 |
| Example of synthesis 16 | / | 0.05 | 2 | 94.8 |
| Example of synthesis 17 | / | 0.05 | 2 | 92.1 |
| Example of synthesis 18 | / | 0.05 | 2 | 98.0 |
| Example of synthesis 19 | / | 0.05 | 2 | 96.4 |
| Example of synthesis 20 | / | 0.05 | 2 | 94.7 |
| Example of synthesis 21 | / | 0.05 | 2 | 97.1 |

Reaction condition: IPA-H₂O(1:1, v/v). 80° C., 3 eq. Base, 1.5 eq. Boronic acid
Conversion ratio (Yield) identified by ¹H NMR 2-2) Reaction between aryliodide and boronic Acid The aryliodide and boronic acid shown in TABLE 6 were allowed to react with each other under the reaction conditions shown in TABLE 6, using the Pd-containing perovskite-like composite oxide produced in Example of production 1 as the catalyst for synthesis reaction. Yields in the respective reactions are shown in TABLE 6.

TABLE 6

| | Aryliodide | Boronic acid | Product | Base | Additive |
|---|---|---|---|---|---|
| Example of synthesis 22 | 2-iodothiophene | PhB(OH)$_2$ | 2-phenylthiophene | K$_2$CO$_3$ | TBAB (1.1 eq) |
| Example of synthesis 23 | 2-iodothiophene | PhB(OH)$_2$ | 2-phenylthiophene | K$_2$CO$_3$ | / |
| Example of synthesis 24 | 4-iodoanisole | 1-(phenylsulfonyl)-1H-indol-3-ylboronic acid | 3-(4-methoxyphenyl)-1-(phenylsulfonyl)-1H-indole | K$_2$CO$_3$ | TBAB (1.1 eq) |
| Example of synthesis 25 | 4-iodoanisole | 1-(phenylsulfonyl)-1H-indol-3-ylboronic acid | 3-(4-methoxyphenyl)-1-(phenylsulfonyl)-1H-indole | K$_2$CO$_3$ | / |
| Example of synthesis 26 | 4-iodoanisole | (E)-styrylboronic acid | (E)-4-methoxystilbene | K$_2$CO$_3$ | / |
| Example of synthesis 27 | 4-iodoanisole | PhB(OH)$_2$ | 4-methoxybiphenyl | K$_2$CO$_3$ | / |
| Example of synthesis 28 | 4-iodofluorobenzene | PhB(OH)$_2$ | 4-fluorobiphenyl | K$_2$CO$_3$ | / |
| Example of synthesis 29 | 4-iodo(trifluoromethyl)benzene | PhB(OH)$_2$ | 4-(trifluoromethyl)biphenyl | K$_2$CO$_3$ | / |

| | Catalyst for synthesis reaction (mol %) | Time (h) | Yield (%) |
|---|---|---|---|
| Example of synthesis 22 | 0.05 | 18 | 89 |
| Example of synthesis 23 | 0.05 | 18 | 61 |
| Example of synthesis 24 | 0.05 | 18 | 70 |
| Example of synthesis 25 | 0.05 | 18 | 70 |

TABLE 6-continued

| | | | | |
|---|---|---|---|---|
| | Example of synthesis 26 | 0.05 | 18 | 92 |
| | Example of synthesis 27 | 0.05 | 5 | 92 |
| | Example of synthesis 28 | 0.05 | 2 | 90 |
| | Example of synthesis 29 | 0.05 | 1 | 92 |

Reaction condition: $LaFe_{0.57}Co_{0.38}Pd_{0.05}O_3$(0.05 mol % Pd), IPA-$H_2O$(1:1, v/v). 80° C., 3 eq. Base, 1.5 eq. Boronic acid
Conversion ratio (Yield) identified by $^1H$ NMR 2-3) Reaction between arylchloride and boronic Acid The arylchloride and boronic acid shown in TABLE 7 were allowed to react with each other under the reaction conditions shown in TABLE 7, using the Pd-containing perovskite-like composite oxide produced in Example of production 1 as the catalyst for synthesis reaction. Yields in the respective reactions are shown in TABLE 7.

TABLE 7

| | Arylchloride | Boronic acid | Product | Base | Additive | Catalyst for synthesis reaction (mol %) | Time (h) | Yield (%) |
|---|---|---|---|---|---|---|---|---|
| Example of synthesis 30 | 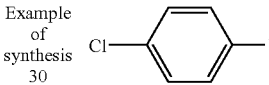 | 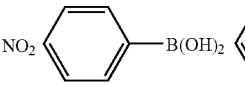 | 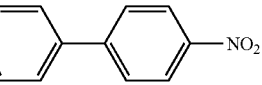 | $Na_2CO_3$ | / | 0.25 | 1 | 71 |

Reaction condition: $LaFe_{0.57}Co_{0.38}Pd_{0.05}O_3$(0.25 mol % Pd), IPA-$H_2O$(1:1, v/v), 135° C.(Microwave heating for 1 hour), 3 eq. Base, 1.5 eq. Boronic acid 2-4) Reaction between arylbromide and boronic Ester The arylbromide and boronic ester shown in TABLE 8 were allowed to react with each other under the reaction conditions shown in TABLE 8, using the Pd-containing perovskite-like composite oxide produced in Example of production 1 as the catalyst for synthesis reaction. Yields in the respective reactions are shown in TABLE 8.

TABLE 8

| | Arylbromide | Boronic ester | Product | Base | Additive | Catalyst for synthesis reaction (mol %) | Time (h) | Yield (%) |
|---|---|---|---|---|---|---|---|---|
| Example of synthesis 31 | 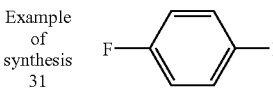 | 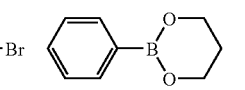 | 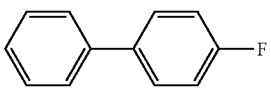 | $K_2CO_3$ | / | 0.05 | 3 | 94 |
| Example of synthesis 32 | 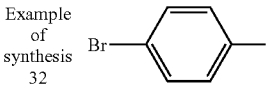 | 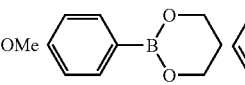 | 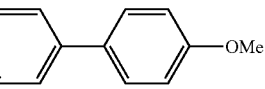 | $K_2CO_3$ | / | 0.05 | 0.05 | 87 |

Reaction condition: $LaFe_{0.57}Co_{0.38}Pd_{0.05}O_3$(0.05 mol % Pd), IPA-$H_2O$(1:1, v/v). 80° C., 3 eq. Base, 1.5 eq. Boronic ester 2-5) Reaction between aryliodide and boronic Ester The aryliodide and boronic ester shown in TABLE 9 were allowed to react with each other under the reaction conditions shown in TABLE 9, using the Pd-containing perovskite-like composite oxide produced in Example of production 1 as the catalyst for synthesis reaction. Yields in the respective reactions are shown in TABLE 9.

TABLE 9

| | Aryliodide | Boronic ester | Product | Base | Additive | Catalyst for synthesis reaction (mol %) | Time (h) | Yield (%) |
|---|---|---|---|---|---|---|---|---|
| Example of synthesis 33 | F—⬡—I | ⬡—B(OCH₂CH₂CH₂O) | F—⬡—⬡ | $K_2CO_3$ | / | 0.05 | 2 | 94 |

Reaction condition: $LaFe_{0.57}Co_{0.38}Pd_{0.05}O_3$ (0.05 mol % Pd), IPA-$H_2O$(1:1, v/v). 80° C., 3 eq. Base, 1.5 eq. Boronic ester 3) Examples of Synthesis by Stille Cross-couplings 3-1) Reaction between arylbromide and trimethylphenyl Tin The arylbromide and trimethylphenyl tin shown in TABLE 10 were allowed to react with each other under the reaction conditions shown in TABLE 10, using the Pd-containing perovskite-like composite oxide produced in Example of production 1 as the catalyst for synthesis reaction. Yields in the respective reactions are shown in TABLE 10.

3-2) Reaction between aryliodide and trimethylphenyl Tin

The aryliodide and trimethylphenyl tin shown in TABLE 11 were allowed to react with each other under the reaction conditions shown in TABLE 11, using the Pd-containing perovskite-like composite oxide produced in Example of production 1 as the catalyst for synthesis reaction. Yields in the respective reactions are shown in TABLE 11.

TABLE 10

| | Arylbromide | Trimethyl-phenyl tin | Product | Base | Additive | Catalyst for synthesis reaction (mol %) | Time (h) | Yield (%) |
|---|---|---|---|---|---|---|---|---|
| Example of synthesis 34 | F—⬡—Br | ⬡—SnMe₃ | F—⬡—⬡ | $K_2CO_3$ | / | 0.05 | 1 | 93 |
| Example of synthesis 35 | Br—⬡—OMe | ⬡—SnMe₃ | ⬡—⬡—OMe | $K_2CO_3$ | / | 0.05 | 1 | 91 |

Reaction condition: $LaFe_{0.57}Co_{0.38}Pd_{0.05}O_3$ (0.05 mol % Pd), $H_2O$, 100° C., 3 eq. Base, 1.5 eq. Trimethylphenyl tin

TABLE 11

| | Aryliodide | Trimethyl-phenyl tin | Product | Base | Additive | Catalyst for synthesis reaction (mol %) | Time (h) | Yield (%) |
|---|---|---|---|---|---|---|---|---|
| Example of synthesis 36 | F—⬡—I | ⬡—SnMe₃ | F—⬡—⬡ | $K_2CO_3$ | / | 0.05 | 1 | 96 |
| Example of synthesis 37 | I—⬡—OMe | ⬡—SnMe₃ | ⬡—⬡—OMe | $K_2CO_3$ | / | 0.05 | 1 | 94 |

Reaction condition: $LaFe_{0.57}Co_{0.38}Pd_{0.05}O_3$ (0.05 mol % Pd), $H_2O$, 100° C., 3 eq. Base, 1.5 eq. Trimethylphenyl tin 4) Examples of Synthesis by Heck Cross-couplings 4-1) Reaction between arylbromide and t-butylacrylate The arylbromide and t-butylacrylate shown in TABLE 12 were allowed to react with each other under the reaction conditions shown in TABLE 12, using the Pd-containing perovskite-like composite oxide produced in Example of production 1 as the catalyst for synthesis reaction. Yields in the respective reactions are shown in TABLE 12.

TABLE 12

| | Arylbromide | tert-butyl-acrylate | Product | Base | Additive | Catalyst for synthesis reaction (mol %) | Time (h) | Yield (%9 |
|---|---|---|---|---|---|---|---|---|
| Example of synthesis 38 | 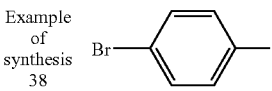 | 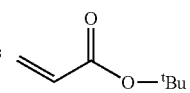 | 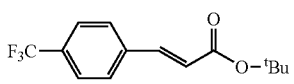 | $K_2CO_3$ | / | 0.25 | 1 | 90 |

Reaction condition: $LaFe_{0.57}Co_{0.38}Pd_{0.05}O_3$ (0.25 mol % Pd), IPA, 100° C., 3 eq. Base, 1.5 eq. tert-butylacrylate 4-2) Reaction between aryliodide and t-butylacrylate The aryliodide and t-butylacrylate shown in TABLE 13 were allowed to react with each other under the reaction conditions shown in TABLE 13, using the Pd-containing perovskite-like composite oxide produced in Example of production 1 as the catalyst for synthesis reaction. Yields in the respective reactions are shown in TABLE 13.

TABLE 13

| | Aryliodide | tert-butyl-acrylate | Product | Base | Additive | Catalyst for synthesis reaction (mol %) | Time (h) | Yield (%9 |
|---|---|---|---|---|---|---|---|---|
| Example of synthesis 39 | 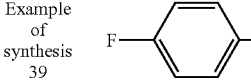 | 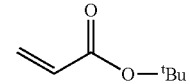 | 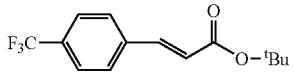 | $K_2CO_3$ | / | 0.25 | 1 | 95 |
| Example of synthesis 40 | 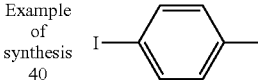 | 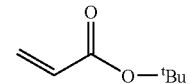 | 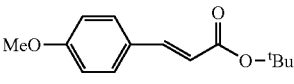 | $K_2CO_3$ | / | 0.25 | 1 | 99 |

Reaction condition: $LaFe_{0.57}Co_{0.38}Pd_{0.05}O_3$ (0.25 mol % Pd), IPA, 100° C., 3 eq. Base, 1.5 eq. tert-butylacrylate 5) Example of Recycle of Catalyst for Synthesis Reaction The arylbromide (4-bromoanisole) and boronic acid (arylbromide) shown in TABLE 14 were synthesized five times repeatedly in the same reaction conditions as in Example of sysnthesis 1 (except change in reaction time). In each synthesis, the catalyst for synthesis reaction was collected through filtration after completion of the reaction and the catalyst for synthesis reaction thus collected was recycled for the following reaction.

TABLE 4

Reaction

| Number of times catalyst is used | 1 | 2 | 3 | 4 | 5 |
|---|---|---|---|---|---|
| Yield(%) | 95 | 93 | 93 | 95 | 93 |
| Reaction time | 1 | 0.6 | 2 | 1 | 1 |

While the illustrative embodiments of the present invention are provided in the above description, such is for illustrative purpose only and it is not to be construed restrictively. Modification and variation of the present invention that will be obvious to those skilled in the art is to be covered by the following claims.

What is claimed is:

1. A synthesizing method for a compound, wherein a compound indicated in a formula (1) given below, and a compound indicated in a formula (2) given below or a compound indicated in a formula (3) given below are allowed to react with each other in the presence of a perovskite-like composite oxide comprising palladium:

$$R_1-X \qquad (1)$$

wherein in formula (1), $R_1$ represents an aryl group that may have a substituent, a heterocyclic group that may have a substituent, or an alkenyl group that may have a substituent, and X represents a halogen atom, a triflouromethanesulfonyloxy group, a p-toluenesulfonyloxy group, or a methanesulfonyloxy group; and $$R_2-M \qquad (2)$$

wherein in formula (2), $R_2$ represents an aryl group that may have a substituent, a heterocyclic group that may have a substituent, or an alkenyl group that may have a substituent, M represents a —B(ORa)$_2$ group or a —Sn(Rb)$_3$ group, Ra represents a hydrogen atom or an alkyl group that may have a substituent, and Rb represents an alkyl group;

wherein as a substitute for Ra, an arylene group that may have a substituent or an alkylene group that may have a substituent may be used as a bonding hand of —OBO—, to form a ring including the —OBO—; and $$R_3HC=CR_4R_5 \qquad (3)$$

wherein in formula (3), $R_3$, $R_4$, and $R_5$ each represent a hydrogen atom, an alkyl group that may have a substituent, an aryl group that may have a substituent, a carboxylic acid derivative, an acid amide derivative, or a cyano group.

2. The synthesizing method for a compound according to claim 1, wherein the compound indicated in the formula (1) and the compound indicated in the formula (2) are allowed to react with each other in the presence of the perovskite-like composite oxide comprising palladium, and wherein in the formula (1), $R_1$ is an aryl group that may have a substituent, and X is a halogen atom, and in the formula (2), $R_2$ is an aryl group that may have a substituent, and M is a —B(ORa)$_2$ group.

3. The synthesizing method for a compound according to claim 1, wherein the perovskite-like composite oxide comprising palladium is represented by a formula (4) given below:

$$AB_{1-x}Pd_xO_3 \qquad (4)$$

wherein in formula (4), A represents at least one element selected from the group consisting of rare-earth elements and alkaline-earth metals, B represents at least one element selected from the group consisting of Al and transition elements except for rare-earth elements and Pd, and x represents an atomic rate of Pd.

4. The synthesizing method for a compound according to claim 1, wherein the perovskite-like composite oxide comprising palladium is represented by a formula (5) given below:

$$A_{1-y}A'_yB_{1-x}Pd_xO_3$$

wherein in formula (5), A represents at least one element selected from rare-earth elements, A' represents at least one element selected from alkaline-earth metals, B represents at least one element selected from the group consisting of Al and transition elements except for rare-earth elements and Pd, x represents an atomic rate of Pd, and y represents an atomic rate of $0 \leqq y \leqq 0.5$.

5. The synthesizing method for a compound according to claim 1, wherein the perovskite-like composite oxide comprising palladium is represented by a formula (6) given below:

$$AB_{1-x}Pd_xO_3 \qquad (6)$$

wherein in formula (6), A represents at least one element selected from the group consisting of Y, La, Ce, Pr and Nd, B represents at least one element selected from the group consisting of Mn, Fe, Co and Al, and x represents an atomic rate of Pd.

* * * * *